(12) United States Patent
Doi et al.

(10) Patent No.: US 8,328,826 B2
(45) Date of Patent: Dec. 11, 2012

(54) PRECURSOR OF A TISSUE REGENERATING INSTRUMENT PROVIDED WITH A SWELLABLE ROD

(75) Inventors: Nobutoshi Doi, Osaka (JP); Shunsuke Notazawa, Osaka (JP)

(73) Assignee: NIPRO Corporation, Osaka (JP)

( * ) Notice: Subject to any disclaimer, the term of this patent is extended or adjusted under 35 U.S.C. 154(b) by 1058 days.

(21) Appl. No.: 11/889,697

(22) Filed: Aug. 15, 2007

(65) Prior Publication Data

US 2008/0288084 A1    Nov. 20, 2008

(30) Foreign Application Priority Data

Aug. 18, 2006 (JP) ................................. 2006-223424

(51) Int. Cl.
*A61B 17/11* (2006.01)
(52) U.S. Cl. ...................................................... 606/152
(58) Field of Classification Search .......... 606/152–155, 606/214, 215; 424/422–426; 623/23.64, 623/1.38, 13.11, 23.71, 13.15, 13.2
See application file for complete search history.

(56) References Cited

U.S. PATENT DOCUMENTS

| | | | | |
|---|---|---|---|---|
| 4,416,028 A | * | 11/1983 | Eriksson et al. | 623/1.38 |
| 4,662,884 A | * | 5/1987 | Stensaas et al. | 606/152 |
| 4,669,474 A | * | 6/1987 | Barrows | 606/152 |
| 4,759,764 A | * | 7/1988 | Fawcett et al. | 623/1.1 |
| 4,870,966 A | | 10/1989 | Dellon et al. | 128/334 R |
| 5,011,486 A | * | 4/1991 | Aebischer et al. | 623/1.15 |
| 5,656,605 A | * | 8/1997 | Hansson et al. | 514/21 |
| 5,735,863 A | | 4/1998 | Della Valle et al. | 606/152 |
| 5,756,457 A | | 5/1998 | Wang et al. | 514/12 |
| 5,830,493 A | | 11/1998 | Yokota et al. | 424/426 |
| 5,834,029 A | | 11/1998 | Bellamkonda et al. | 424/570 |
| RE36,370 E | | 11/1999 | Li | 424/443 |
| 6,090,117 A | | 7/2000 | Shimizu | 606/152 |
| 6,156,575 A | | 12/2000 | Fassbind et al. | 435/395 |
| 6,214,021 B1 | | 4/2001 | Hadlock et al. | 606/152 |

(Continued)

FOREIGN PATENT DOCUMENTS

EP    0 945 145 A1    9/1999

(Continued)

OTHER PUBLICATIONS

Rosen, Joseph M. et al., "Fascicular Sutureless and Suture Repair of the Peripheral Nerves", *Orthopaedic Review*, vol. VIII, No. 4, 1979, pp. 85-92.

(Continued)

*Primary Examiner* — Julian Woo
*Assistant Examiner* — Christopher L Templeton
(74) *Attorney, Agent, or Firm* — Kubovcik & Kubovcik

(57) ABSTRACT

The present invention provides a precursor for producing a tissue regenerating instrument that regenerates a tissue, including: a tube made of a biodegradable material provided with a lumen in a longitudinal direction; a rod made of a biodegradable material swellable with a softening solvent, fixed to an inner wall of the tube substantially parallel to the longitudinal direction of the tube; and an adhesive that fixes the rod to the inner wall of the tube, in which the rod in a non-swelled state has an occupied cross-sectional area perpendicular to the longitudinal direction that is smaller than a cross-sectional area of the lumen of the tube, and the occupied cross-sectional area perpendicular to the longitudinal direction of the rod in a saturated swelled state with the softening solvent is substantially the same as the cross-sectional area of the lumen of the tube.

10 Claims, 8 Drawing Sheets

U.S. PATENT DOCUMENTS

| | | | |
|---|---|---|---|
| 6,589,257 B1 * | 7/2003 | Shimizu | 606/152 |
| 6,596,296 B1 * | 7/2003 | Nelson et al. | 424/426 |
| 6,953,482 B2 * | 10/2005 | Doi et al. | 623/23.71 |
| 7,198,799 B2 * | 4/2007 | Mueller et al. | 424/426 |
| 7,615,063 B2 * | 11/2009 | Doi et al. | 606/152 |
| 2002/0161450 A1 | 10/2002 | Doi et al. | 623/23.71 |
| 2004/0170664 A1 * | 9/2004 | Spector et al. | 424/426 |
| 2006/0184185 A1 * | 8/2006 | Olausson et al. | 606/152 |
| 2006/0235534 A1 * | 10/2006 | Gertzman et al. | 623/17.16 |
| 2007/0232169 A1 * | 10/2007 | Strickler et al. | 442/181 |

FOREIGN PATENT DOCUMENTS

| | | |
|---|---|---|
| JP | 5-237139 A | 9/1993 |
| WO | 88/06871 A1 | 9/1988 |
| WO | 02/47557 A1 | 6/2002 |

OTHER PUBLICATIONS

Reid, R. L. et al.; "Biodegradable Cuff an Adjunct to Peripheral Nerve Repair: A Study in Dogs"; *The Hand;* vol. 10, No. 3, pp. 259-266; 1978.

Henderson, C. E. et al.; "Denervation Increases a Neurite-promoting Activity in Extracts of Skeletal Muscle"; *Nature;* vol. 302, pp. 609-611; 1983.

Mackinnon, S. E.; "Nerve Regeneration Through a Pseudosynovial Sheath in a Primate Model"; *Plastic and Reconstructive Surgery;* vol. 75, No. 6, pp. 833-839; 1985.

Nishimune, H. et al.; "Neurocrescin: A Novel Neurite-outgrowth Factor Secreted by Muscle After Denervation"; *NeuroReport;* vol. 8, pp. 3649-3654; 1997.

Ochi, M. et al.; "Promotion of Sciatic Nerve Regeneration in Rats by a New Neurotrophic Pyrimidine Derivative MS-430"; *Gen. Pharmac.;* vol. 26, No. 1, pp. 59-64; 1995.

Mackinnon, S. E. et al.; "Clinical Nerve Reconstruction with a Bioabsorbable Polyglycolic Acid Tube"; *Plastic and Reconstructive Surgery;* vol. 85, No. 3, pp. 419-424; 1990.

Aebischer, P. et al.; "Regeneration of Transected Sciatic Nerves Through Semi-Permeable Nerve Guidance Channels"; *Trans Am Soc Artif Intern Organs;* vol. XXXII, pp. 474-477; 1986.

McDonald, J. W.; "Transplanted Embryonic Stem Cells Survive, Differentiate and Promote Recovery in Injured Rat Spinal Cord"; *Nature Medicine;* vol. 5, No. 12, pp. 1410-1412; 1999.

Uyeda, A. et al.; "MDP77: A Novel Neurite-Outgrowth-Promoting Protein Predominantly Expressed in Chick Muscles"; *Biochemical and Biophysical Research Communications;* vol. 269, pp. 564-569; 2000.

Pu, L. et al.; "Effects of Nerve Growth Factor on Nerve Regeneration Through a Vein Graft Across a Gap"; *Plastic and Reconstructive Surgery;* vol. 104, No. 5, pp. 1379-1385; 1999.

Rosen, J. M. et al.; "Fascicular Tubulization: A Cellular Approach to Peripheral Nerve Repair"; *Annals of Plastic Surgery;* vol. 11, No. 5, pp. 397-411; 1983.

Terada, N. et al. "Bioartificial Nerve Grafts Based on Absorbable Guiding Filament Structures—Early Observations"; *Scand J Plast Reconstr Hand Surg;* vol. 31, pp. 1-6; 1997.

Henderson, C. E. et al.; "Neurite Outgrowth from Embryonic Chicken Spinal Neurons is Promoted by Media Conditioned by Muscle Cells"; *Proc. Natl. Acad. Sci.;* vol. 78, No. 4, pp. 2625-2629; 1981.

Gibson, K. L. et al.; "Comparison of Sciatic Nerve Regeneration Through Silicone Tubes and Nerve Allografts"; *Microsurgery;* vol. 10, pp. 126-129; 1989.

Molander, H. et al.; "Nerve Repair Using a Polyglactin Tube and Nerve Graft: An Experimental Study in the Rabbit"; *Biomaterials;* vol. 4, pp. 276-280; 1983.

Aebischer, P. et al.; "Blind-ended Semipermeable Guidance Channels Support Peripheral Nerve Regeneration in the Absence of a Distal Nerve Stump"; *Brain Research;* vol. 454, pp. 179-187; 1988.

Lundborg, G. et al.; "Regeneration of Peripheral Nerve Through a Preformed Tissue Space. Preliminary Observations on the Reorganization of Regenerating Nerve Fibres and Perineurium"; *Brain Research;* vol. 178, pp. 573-576; 1979.

Lundborg, G. et al.; "Bioartificial Nerve Grafts"; *Scand J Plast Reconstr Hand Surg;* vol. 30, pp. 105-110; 1996.

Nyilas, E. et al.; "Synthetic Bioresorbable Polymers: I. Polyester and Polyester Composite Guidance Channels for Peripheral Nerve Repair"; *9th Annual Meeting of the Society for Biomaterials;* 1983.

Lee, G. et al.; "Experimental Study of a Nerve Guide-Tube Made from Dehydrothemally Treated Gelatin Application to Repair of Gap in Rat Sciatic Nerve"; *J. Artif. Organs. (Jinkoh Sohki);* vol. 22, No. 2, pp. 364-369; 1993.

Sunderland, S.; "A Classification of Peripheral Nerve Injuries Producing Loss of Function"; *Brain;* vol. 74, No. 4, pp. 491-516; 1951.

Wakabayashi, Y. et al.; "Regeneration of Motor Nerve"; *Inflammation and Immunity;* vol. 9, No. 3, pp. 271-277; 2001.

Itoh, S. et al.; "Regeneration of Motion Nerve and Artificial Nerve"; *Modern Treatment;* vol. 31, No. 12, pp. 115-123; 1999.

Wakabayashi, Y. et al.; "Artificial Nerve for Regeneration of Motion Nerve"; *Clinical Neuroscience;* vol. 18, No. 11, pp. 1280-1283; 2000.

Archibald, S. J. et al.; "A Collagen-Based Nerve Guide Conduit for Peripheral Nerve Repair: An Electrophysiological Study of Nerve Regeneration in Rodents and Nonhuman Primates"; *The Journal of Comparative Neurology;* vol. 306, pp. 685-696; 1991.

Itoh, S. et al.; "Synthetic Collagen Fibers Coated with a Synthetic Peptide Containing the YIGSR Sequence of Laminin to Promote Peripheral Nerve Regeneration in vivo"; *Journal of Materials Science: Materials in Medicine;* vol. 10, pp. 129-134; 1999.

Tong, X. et al.; "Sciatic Nerve Regeneration Navigated by Laminin-Fibronectin Double Coated Biodegradable Collagen Grafts in Rats"; *Brain Research,* vol. 663, pp. 155-162; 1994.

Colin, W. et al.; "Nerve Regeneration Through Collagen Tubes"; *J. Dent. Res.,* vol. 63(7), pp. 987-993; 1984.

Itoh, S. et al.; "A Study on Induction of Nerve Regeneration Using Bioabsorbable Tubes"; *J. Jpn. Soc. Surg. Hand.;* vol. 17(4), pp. 371-375; 2000.

Suzuki, K. et al.; "Development of PGA-Collagen Channel for Peripheral Nerve Regeneration-Functional Evaluation"; *Jpn. J. Artif. Organs;* vol. 27(2), pp. 490-494; 1998.

Kiyotani, T. et al.; "Peripheral Nerve Regeneration in a PGA-Collagen Composite Tube"; *Jpn J. Artif. Organs;* vol. 25(2), pp. 476-480; 1996.

Shimada, H. et al.; "Induction of Peripheral Nerve Regeneration Using Laminin-Fibronectin Double Coated Collagen Fiber Grafts"; *Jpn. J. Artif. Organs;* vol. 22(2), pp. 359-363; 1993.

Kline, D. G. et al.; "The Use of a Resorbable Wrapper for Peripheral-Nerve Repair"; *Journal of Neurosurgery;* vol. 21(9), pp. 737-750; 1964.

\* cited by examiner

PRECURSOR OF A TISSUE REGENERATING INSTRUMENT PROVIDED WITH A SWELLABLE ROD

BACKGROUND OF THE INVENTION

1. Field of the Invention

The present invention relates to a precursor of a tissue regenerating instrument and to a method of producing a tissue regenerating instrument.

2. Description of the Related Art

When a tissue such as a nerve or tendon of a human is damaged due to an accident, a disaster or a disease and can not be healed by self resilience, disorders in perception, sensation, and exercise capacity of a patient is occurred. To such a patient, a medical care may be performed in which after the damaged portion is excised, a tissue is collected from another site of the body of the patient and transplanted to the excised portion. Such an operation is called autotransplantation. Since in autotransplantation a healthy tissue which is not damaged is collected, the extracted portion may cause disorders in perception, sensation and mobility in the site.

Accordingly, various studies have been developed with medical cures in which an instrument provided with a foothold for cell growth is implanted in the excised site to allow cells to grow from an end of the tissue along the foothold, thereby regenerating the tissue and recovering the function of the tissue. These are studies as part of so-called regenerative medicine and such an instrument is called scaffold. The instrument includes, as a major construction, a tube that prevents other cells from invading from outside and a guiding member that is inserted in the lumen of the tube and guides nerve cells to grow in a longitudinal direction.

In studies of regenerative medicine using a scaffold, one skilled in the art would consider incorporating a drug or cell in the instrument, who relies on a special function of cells without thorough consideration. However, such an instrument having incorporated therein a drug or cells not only increases cost prices of the instrument but also requires physicians with extra efforts from the viewpoint of storage and safety management. Further, physicians must have knowledge and technique to handle the drug or cell. Therefore, those physicians who have no such knowledge and technique can not handle the instruments.

For example, the nerve regenerating tube described in WO 1998/022155 is very difficult to handle since the tube uses a gel containing collagen, laminin or the like. This is because gel is fluid and has an unstable shape. Further, since the moisture in the gel penetrates into collagen, the collagen is decomposed even if the collagen is crosslinked. In such cases, the instrument can not be stored for a long period of time.

Further, the nerve regeneration tube described in JP 2005-143979 A is seeded with Schwann cell. This can be handled only by physicians who have knowledge and technique for handling cells.

In view of the present state of the above-mentioned regenerative medicine, the inventors of the present invention have made extensive studies on development of regeneration instruments that do not handle cells. As a result, they have invented a collagen-made tissue regenerating instrument (JP 2002-320630 A). Such an instrument is wholly constituted by collagen, a material which is decomposed and absorbed in a living organism and in addition uses no compound such as a crosslinking agent, so that the instrument is safely decomposed and absorbed in a living organism. Further, surprisingly, the instrument allows a tissue to be regenerated without incorporating a special cell. That is, there is no need to handle a drug or cell, so that manufacturers can produce this instrument at low cost. Further, the produced instrument will not be decomposed or deteriorated for a long period of time. Any physician who has a general surgery technique can easily perform treatment with this instrument.

Next problem in development of this instrument is to improve added value by improving handleability. Thus, the improvement of additional value does not mean incorporation of a drug or cell in the instrument as described above, but improvement in the handleability of the instrument. Here, an instrument having a shape which is the easiest for physicians to handle may be an instrument having a collagen tube provided with a lumen therein, with a space being provided in both ends of the lumen.

For example, if the instrument is flat on both ends of the instrument as described in WO 1998/022155 and JP 2005-143979 A, physicians must use end-to-end suture, which is an extremely high level technique of suture, to suture the instrument and the tissue. In addition, when the instrument and the tissue are sutured, an end of the instrument and an end of the tissue are just in abutment, so that there is the possibility that the cells of the tissue may grow on outer wall of the instrument.

On the other hand, if an instrument provided with a space for inserting a tissue end in each lumen in advance is produced, the length of the tissue to be regenerated is not constant, so that the instrument can be used only for regeneration of a limited tissue. For this reason, the instrument must be cut so as to match the length of the tissue to be regenerated. However, of course, the cut surface is flat.

The inventors of the present invention have disclosed a nerve regeneration inducing tube having a space in which a tissue end is inserted on at least one end of the tube (JP 2004-208808 A). Such an instrument is cut so as to match the length of a nerve to be regenerated. The instrument can be implanted after an end of a nerve on the side of the central nerve is inserted in the space. However, the end of the nerve on the peripheral nerve end will be for a flat end. Since no cell grows from the peripheral nerve, the bad effect that cells grow on the outer surface of the instrument can be prevented but still end-to-end suture must be performed for suturing a nerve and an instrument.

Generally, such an instrument may be improved in handleability of the instrument by swelling with a softening solution such as physiological saline before implantation. However, in the instruments disclosed in above-mentioned Patent Documents, the inducing member is fully packed in the lumen of the tube, the penetration rate of the softening solution such as physiological saline is insufficient, so that it takes a long time until saturated swelling state is reached. Further, the inducing member has an outer diameter larger than an inner diameter of the tube by swelling, so that the tube may be deformed or broken. Even when the tube is not deformed or broken, high friction occurs between the inner wall of the tube and the inducing member, which makes difficult production of an instrument provided with a space for inserting a tissue end in the lumen on both ends.

In addition, there arises also the problem that when the inducing member is packed in the lumen of the tube, operation of inserting the inducing member in the lumen of the tube is cumbersome in the production step of the instrument. In particular, the inducing member in the instrument disclosed in Patent Document 2 is a bundle of a plurality of filaments, so that the ends of the inducing members is not aligned. Therefore, during the operation of inserting the inducing member in the lumen of the tube, a portion of the filament bundle could get hung on an end of the tube, which makes the operation cumbersome.

BRIEF SUMMARY OF THE INVENTION

It is an object of the present invention to facilitate production of a precursor for producing a tissue regenerating instrument and make the production of the tissue regenerating instrument from the precursor more simple and more easy.

As a result of extensive studies, the inventors of the present invention focused attention to use of a tissue generating instrument after immersing the instrument in a softening solution such as physiological saline to swell upon implantation of the tissue regenerating instrument in order to improve the handleability of the instrument, and to swelling property of the instrument with the softening solution such as physiological saline and have completed the present invention.

The present invention relates to:

[1] A precursor for producing a tissue regenerating instrument that regenerates a tissue, comprising:

a tube made of a biodegradable material provided with a lumen in a longitudinal direction;

a rod made of a biodegradable material swellable with a softening solvent, fixed to an inner wall of the tube substantially parallel to the longitudinal direction of the tube; and a fixing means that fixes the rod to the inner wall of the tube, wherein the rod in a non-swelled state has an occupied cross-sectional area perpendicular to the longitudinal direction is smaller than a cross-sectional area of the lumen of the tube, and the occupied cross-sectional area perpendicular to the longitudinal direction of the rod in a saturated swelled state with the softening solvent is substantially the same as the cross-sectional area of the lumen of the tube;

[2] The precursor of a tissue regenerating instrument according to [1], wherein the softening solvent is physiological saline;

[3] The precursor of a tissue regenerating instrument according to [1], wherein the rod is substantially a circular column;

[4] The precursor of a tissue regenerating instrument according to [1], wherein the rod comprises a bundle of a plurality of threads made of a biodegradable material arranged substantially in parallel, at least portions of adjacent threads being adhered to each other;

[5] The precursor of a tissue regenerating instrument according to [1], wherein the rod has a longitudinal length shorter than a longitudinal length of the tube by a tissue insertion space forming length (D), and wherein one end of the tube and one end of the rod are aligned with each other;

[6] The precursor of a tissue regenerating instrument according to [1], wherein the fixing means is provided on at least a portion of the inner wall of a region to be excised of the tube.

[7] The precursor of a tissue regenerating instrument according to [4], wherein the rod has a longitudinal length shorter than a longitudinal length of the tube by a tissue insertion space forming length (D), and wherein one end of the tube on the side of a region to be excised and one end of the rod are aligned with each other;

[8] The precursor of a tissue regenerating instrument according to [1], wherein the fixing means comprises a hydrophilic polymer;

[9] The precursor of a tissue regenerating instrument according to [1], wherein the fixing means comprises an adhesive;

[10] The precursor of a tissue regenerating instrument according to [9], wherein the adhesive comprises a biodegradable material;

[11] A method of producing a tissue regenerating instrument for regenerating a linear tissue from a precursor of the tissue regenerating instrument, wherein the precursor of the tissue regenerating instrument comprising:

a tube made of the biodegradable material provided with a lumen in a longitudinal direction;

a rod made of the biodegradable material swellable with a softening solvent, fixed to an inner wall of the tube substantially parallel to the longitudinal direction of the tube; and a fixing means that fixes the rod to the inner wall of the tube, wherein the rod in a non-swelled state has an cross-sectional area perpendicular to the longitudinal direction is smaller than a cross-sectional area of the lumen of the tube, and the occupied cross-sectional area perpendicular to the longitudinal direction of the rod in a saturated swelled state with the softening solvent is substantially the same as the cross-sectional area of the lumen of the tube, the method of producing a tissue regenerating instrument comprising the steps of:

(1) immersing the precursor of the tissue regenerating instrument in a softening solvent to swell the precursor of the tissue regenerating instrument;

(2) releasing the fixing means to make the rod slidable in the inner lumen of the tube;

(3) excising a portion of the precursor so that the longitudinal length of the precursor is a sum of a length of a tissue to be regenerated and a tissue insertion space forming length (D);

(4) excising a portion of the rod to make a longitudinal length of the precursor shorter than a longitudinal length of the tube by a tissue insertion space forming length (D); and (5) arranging the rod in the center of the tube to form a tissue insertion space in a lumen on both ends of the tube;

[12] The method of producing a tissue regeneration instrument according to [11], wherein the longitudinal length of the rod of the precursor is shorter than the longitudinal length of the tube of the precursor by the tissue insertion space forming length (D), and one end of the tube of the precursor and one end of the rod of the precursor are aligned, and wherein the step (3) and the step (4) are performed simultaneously.

[13] The method of producing a tissue regeneration instrument according to [12], wherein the softening solvent is physiological saline and the fixing means of the precursor comprises a hydrophilic polymer, and wherein the step (1) and the step (2) are performed simultaneously;

[14] A tissue regenerating instrument produced from a precursor of the tissue regenerating instrument, wherein the precursor of the tissue regenerating instrument comprising:

a tube made of a biodegradable material provided with a lumen in a longitudinal direction;

a rod made of a biodegradable material swellable with a softening solvent, fixed to an inner wall of the tube substantially parallel to the longitudinal direction of the tube; and a fixing means that fixes the rod to the inner wall of the tube, wherein the rod in a non-swelled state has an occupied cross-sectional area perpendicular to the longitudinal direction is smaller than a cross-sectional area of the lumen of the tube, and the occupied cross-sectional area perpendicular to the longitudinal direction of the rod in a saturated swelled state with the softening solvent is substantially the same as the cross-sectional area of the lumen of the tube, the tissue regenerating instrument being produced by a method of producing a tissue regenerating instrument comprising the steps of:

(1) immersing the precursor of the tissue regenerating instrument in a softening solvent to swell the precursor of the tissue regenerating instrument;

(2) releasing the fixing means to make the rod slidable in the inner lumen of the tube;

(3) excising a portion of the precursor, so that the longitudinal length of the precursor is a sum of a length of a tissue to be regenerated and a tissue insertion space forming length (D);

(4) excising a portion of the rod to make a longitudinal length of the precursor shorter than a longitudinal length of the tube by a tissue insertion space forming length (D); and (5) arranging the rod in the center of the tube to form a tissue insertion space in a lumen on both ends of the tube.

The precursor of the tissue regenerating instrument of the present invention can facilitate production of a tissue regenerating instrument provided with a space for inserting a tissue on both ends thereof. Therefore, physicians can implant such an instrument easily without special techniques.

Figure 1:
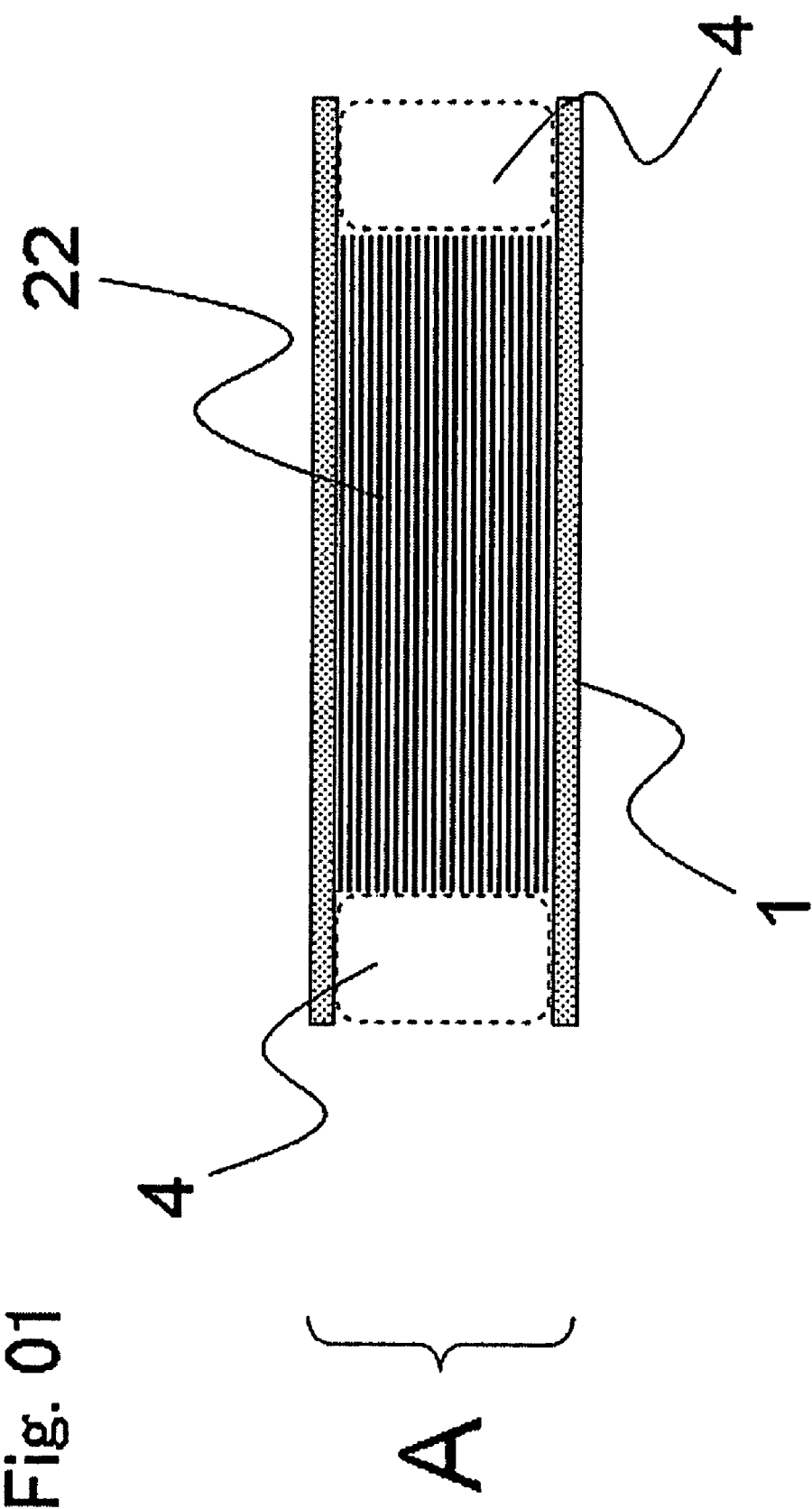
FIG. 1 is a diagram showing a tissue regenerating instrument A, which is a final object of the present invention.

1 tube
21 rod (in non-swelled state)
22 rod in saturated swelled state
31 fixing means in first embodiment
32 fixing means in second embodiment
4 tissue insertion space
5 fluid passage
6 flat end
7 space portion
A tissue regenerating instrument
B, B1~B4, B', B'1, B'2 PRECURSOR OF TISSUE REGENERATING INSTRUMENT

DETAILED DESCRIPTION OF THE INVENTION

Hereinafter, the present invention is described with reference to the attached drawings. FIG. 1 is a diagram showing a tissue regenerating instrument A having provided a tissue inserting section on both ends thereof, which is a final object of the present invention.

"Tissue regenerating instrument" refers to an instrument having a longitudinal direction to be implanted in a living organism for connecting dissevered tissue ends to each other, both ends of which form tissue insertion spaces 4. Also, the tissue regenerating instrument refers to an instrument used in the field of regenerative medicine such that after implantation of the instrument, the damaged tissue regenerates along the longitudinal direction of the instrument but the instrument itself is digested and absorbed.

The tissue targeted by the present invention is not particularly limited as far as it is a tissue that can regenerate by the capacity for regeneration of a human body. For example, a nerve, a tendon, a ligament, a blood vessel, and an esophagus may be exemplified. In particular, the tissue regenerating instrument of the present invention is preferably used in regeneration of a nerve, tendon, and ligament.

"Tissue inserting section" refers to a space formed between both ends of the tissue regenerating instrument A for connecting the tissue regenerating instrument A and tissue ends. The longitudinal length of the tissue inserting section 4, which can be appropriately determined by one skilled in the art depending on the type of the tissue to be regenerated, is not particularly limited. For example, in the case of a nerve, the length of the nerve is about 2 mm to about 40 mm, preferably about 2 mm to about 10 mm from the viewpoint of facilitating insertion of the nerve. In the case of tendon, the length of the tendon is about 2 mm to about 60 mm, preferably about 5 mm to about 30 mm from the viewpoint of facilitating insertion of the tendon. Further, in the case of ligament, the length of ligament is about 2 mm to about 60 mm, preferably about 5 mm to about 30 mm from the viewpoint of facilitating insertion of the ligament. Provision of the tissue inserting section 4 facilitates connection without requiring special suturing technique in connecting the tissue regenerating instrument A and the tissue ends and prevents growth of tissue cells toward neighboring tissues.

Figure 2:
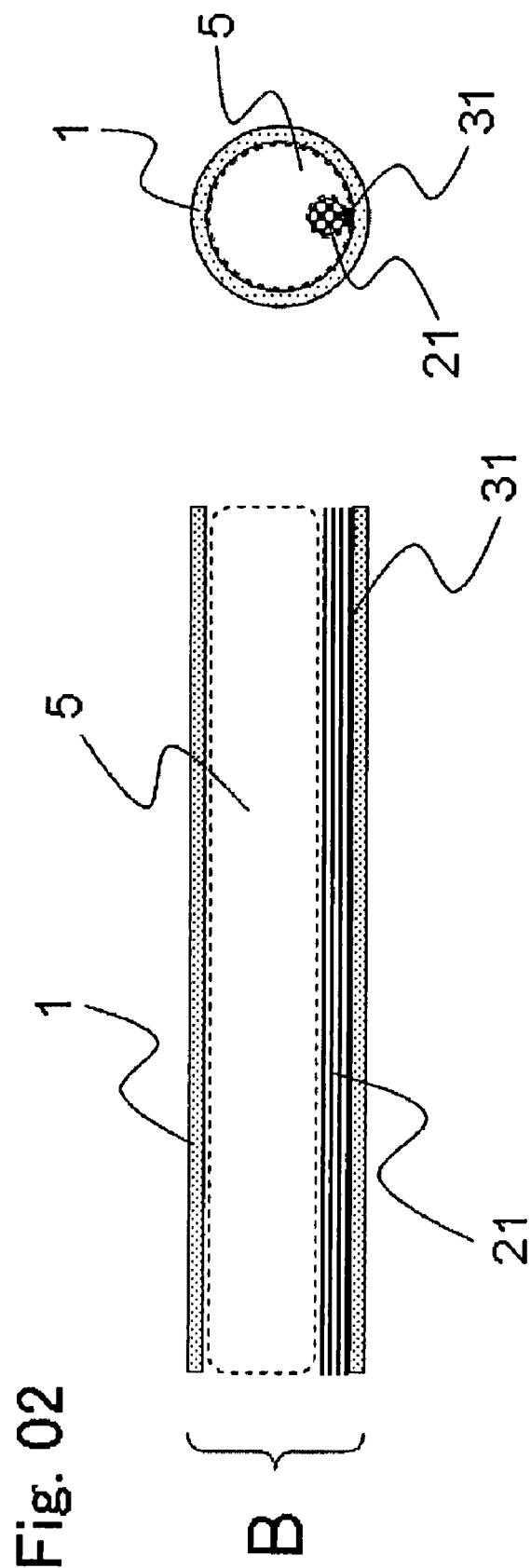
FIG. 2 is a diagram illustrating an embodiment (B) of the precursor of the tissue regenerating instrument of the present invention.

The present invention provides a precursor B for producing the tissue regenerating instrument A as shown in FIG. 1. FIG. 2 is a diagram illustrating an embodiment of the precursor B of the tissue regenerating instrument of the present invention. The precursor B of the tissue regenerating instrument is provided with a lumen in the longitudinal direction and includes a tube 1 made of a biodegradable material, a rod 21 made of a biodegradable material provided in the lumen of the tube 1, and fixing means 31 and 32 that fix the rod 21 to the tube 1.

"Precursor of a tissue regenerating instrument" refers to a thing produced by a physician for use in producing a target tissue regenerating instrument A depending on the state of damage of the tissue of a patient. In the present invention, the precursor B of the tissue regenerating instrument may be abbreviated as "precursor". A method of producing the tissue regenerating instrument A from the precursor B may include, for example, metering of the length of the damaged tissue, metering of the length of the instrument, cutting of the instrument, swelling of the instrument and deformation of the instrument. These are described hereinbelow.

Upon producing a tissue regenerating instrument A from a precursor B, the precursor B is immersed and swelled in a softening solvent in order to improve the handleability thereof. "Non-swelled state" refers to a state before immersing and swelling in the solution and "saturated swelled state" refers to a state in which the precursor B is immersed in the solution and the swelling is saturated. The immersion and swelling in the present invention are performed using a softening solvent under conditions of atmospheric pressure, at a humidity of 60% and 25 to 40° C.

"Softening solvent" refers to a solution that softens the precursor B of the tissue regenerating instrument. Although physiological saline is mainly used as the softening solvent, the softening solvent is not particularly limited thereto. "Physiological saline" refers to 0.9 wt % aqueous sodium chloride solution, which is substantially isotonic with the body fluid of a human. The time until swelling reaches saturation depends on the material of the precursor B. The relation between the sate of saturated swelling and the material of the precursor B is described hereinbelow.

<Tube>

"Tube" refers to a structure that prevents tissue cells from growing toward neighboring tissues. The shape of the tube 1 includes cylindrical (tubular), and prismatic (trigonal, tetragonal, pentagonal, and hexagonal). In particular, from the viewpoint of ease of production, cylindrical (tubular) shape is preferable but the present invention is not limited thereto.

The longitudinal length of the tube 1 depends on biological classification of subject, i.e., patient human or animal, body shape and type of tissue and hence is not particularly limited. However, it is preferable that the longitudinal length of the tube 1 is sufficiently larger than the length of a cut tissue that one skilled in the art can expect. The length of a cut tissue that one skilled in the art can expect is, for example, about 1 mm to about 300 mm when the tissue is a human median nerve. When the tissue is a human sciatic nerve is about 1 mm to about 500 mm.

Therefore, for example, in the case where the tissue is a human nerve, the longitudinal length of the tube 1 may be about 5 mm or more from the viewpoint of applicability to regeneration of all human nerves. From the viewpoint of suppressing an increase in production cost due to use amount of raw material, the longitudinal length of the tube 1 is preferably about 10 mm to about 200 mm. For example, in the case where the tissue is a human ligament, the longitudinal length of the tube may be about 5 mm or more, preferably about 10 mm to about 100 mm.

On the other hand, the inner diameter of the tube 1 may be appropriately set by one skilled in the art based on the tissue to be regenerated and is not particularly limited. For example, in the case where the tissue is a nerve, the inner diameter of the tube 1 is about 1 mm to about 20 mm, preferably about 1 mm to about 10 mm from the viewpoint of the possibility that the frequency of use of the tissue regenerating instrument is highest. On the other hand, when the tissue is, for example, a human tendon, the inner diameter of the tube 1 is about 1 mm to about 30 mm, preferably about 1 mm to about 20 mm. When the tissue is, for example, a human ligament, the inner diameter of the tube 1 is about 1 mm to about 20 mm, preferably about 1 mm to about 10 mm.

Since the tube 1 is used in regenerative medicine, the tube 1 is made of a biodegradable material. The biodegradable material refers to a material that is decomposed by itself, preferably absorbed after decomposition when the biodegradable material is implanted in a living organ. For example, polylactic acid, polyglycolic acid, $\epsilon$-aminocaprolactone, collagen, and chitosan may be exemplified. Among these materials, collagen is preferred from the viewpoint that no inflammatory reaction is caused and decomposition and absorption can be controlled by crosslinking treatment.

"Collagen" refers to a major protein component that constitutes a connective tissue in animals, and the structure of main chain is constituted by (Gly-X-Y), (Gly-Pro-X), and (Gly-Pro-Hyp). Here, X and Y represent each a natural or non-natural amino acid other than glycine, proline or hydroxyproline.

The types of collagen include I, II, and III. In particular, I and III are preferred from the viewpoint of easy handling but collagen is not limited thereto. The collagen used in the present invention includes gelatin, which is thermally modified collagen. From the viewpoint of cell adhesion, collagen is preferable.

Collagen can be produced by extraction, chemical peptide synthesis, and recombinant DNA method. At the time of filing the present application, collagen obtained by extraction from a living tissue from the viewpoint of production cost. Further, the living tissues may be derived from, for example, oxen, pigs, rabbits, sheep, rats, birds, fish, and humans. Examples of the living organism tissue include skin, tendon, bone, cartilage and internal organs of the animals described above. One skilled in the art can select these appropriately and the present invention is not limited to these.

Further, from the viewpoint of facilitating industrial production, it is preferable that collagen treated to be soluble in solvents is selected. For example, solubilized collagens such as enzyme-solubilized collagen, acid-solubilized collagen, alkali-solubilized collagen, and neutral-solubilized collagen may be exemplified. In particular, from the viewpoint of easy handling, acid-solubilized collagen is preferable. From the view point of the safety upon the implantation is living organism, atelocollagen, which is a collagen subjected to treatment of removing a telopeptide, an antigen-determinant group, is preferable.

Here, production of the tube 1 is described. However, production conditions, etc. can be appropriately set by one skilled in the art, the present invention is not limited to the following description.

Here, the method of producing the tube 1 includes, for example, (i) a method of directly molding into the tube 1 by an industrial production method such as injection molding, compression molding and extrusion molding, (ii) producing a membrane substance such as film, woven fabric and non-woven fabric and molding the membrane substance into a tube, and (iii) a method of producing a monofilament by a spinning method and molding the monofilament into a tube. These production methods can be appropriately set by one skilled in the art depending on the raw materials of the tube 1. For example, when the raw material is collagen, (iii) the method of producing a monofilament by a spinning method or the like and molding the monofilament to a tube is preferable from the viewpoint of easy production and low production cost.

The monofilament may be those produced by a wet spinning method, a dry spinning method, and a melt spinning method. For example, when the raw material is collagen, one produced by a wet spinning method is preferably from the viewpoint of easy production and low production cost.

The wet spinning method is performed, for example, by discharging an aqueous solution of a biodegradable polymer in a coagulation bath using a gear pump, a dispenser and various pumping devices. To perform uniform spinning, a dispenser is preferable from the viewpoint of exhibiting less pulsation to discharge a constant amount of a solution stably. The aperture of discharge nozzles is about 10 µm to about 200 µm, preferably about 50 µm to about 150 µm from the viewpoint of further increasing the strength of monofilament. Further, the concentration of the aqueous solution is about 0.1 wt % to about 20 wt %, preferably about 1 wt % to about 10 wt % from the viewpoint of the strength of the monofilament.

The solvent of the coagulation bath used the wet spinning is not particularly limited as far as the solvent is a solvent, a suspension, an emulsion, and a solution that coagulate the biodegradable polymer. For example, when collagen is used as a raw material for a thread, inorganic salt aqueous solutions, inorganic salt-containing organic solvents, alcohols, and ketones can be exemplified. Examples of the inorganic salt aqueous solution include sodium sulfate, sodium chloride, ammonium sulfate, calcium chloride, and magnesium chloride. Solutions obtained by dissolving or dispersing the inorganic salts in alcohols or acetones may be used. Examples of the alcohols include methanol, ethanol, isopropanol, amyl alcohol, pentanol, hexanol, and ethylene glycol. Examples of the ketones include acetone and methyl ethyl ketone. Among these, ethanol and sodium chloride-dispersed ethanol dispersion are preferably used from the viewpoint of high strength of the spun filament.

The thread of biodegradable material discharged in coagulation bath is taken up from the coagulation bath and passed through a drying step and wound around a cylindrical column to be molded as a tube 1. Here, the drying step may be performed under conditions such that the collagen is no thermally denatured, the droplets from the coagulation bath attached to the periphery of the monofilament are removed, and the monofilament is not broken. In this case, it is preferable that the solvent remains more or less in the inside of the monofilament. This is because the remaining solvent drips outside after minding the monofilament around the cylindrical column. The dripped solvent dissolves a part of the monofilament, thereby allowing adhesion of adjacent monofilaments to each other. Drying monofilaments such that adjacent monofilaments are adhered to each other in this manner enables formation of the tube 1 having a further increased strength. The drying method that satisfies the above-mentioned conditions includes, for example, a method of drying by supplying air under conditions of spinning speed (winding up speed or drawing speed) of about 10 m/min to about 10,000 m/min, a humidity of about 50% or less, and a temperature of 43° C. or less when an aqueous collagen solution is discharged and spun in a coagulation bath of ethanol.

As a method of producing the tube 1, there is a method of winding a monofilament around a cylindrical column many times, thereby forming a plurality of layers. In this case, the winding density of monofilament in at least one layer which is different from the winding density of other layers make in a further increase in strength of the tube 1. In the present invention, winding density refers to a number of times of winding per unit length of the tube 1 in the longitudinal direction. For example, it is preferable that the winding density of at least one layer is set less than 10 times/cm, and the winding density of the monofilament in other layers is set 10 to 30 times/cm. For details, reference is made to the disclosure of Japanese Patent Application Laid-open No. 2004-073221.

Also, by coating a biodegradable material solution on a side wall of the tube 1 and drying the coating, the strength of the tube 1 is increased. The biodegradable material used in this treatment is preferably the same material as the material of the tube 1 from the viewpoint of increasing adhesion to the material of the tube 1. The concentration of the biodegradable material solution is, for example, about 0.1% to about 20% (w/w), preferably about 1% to about 10% (w/w) from the viewpoint of easy handling when the biodegradable polymer is collagen.

Preferably, the tube 1 is further subjected to crosslinking treatment as necessary. The crosslinking treatment enables in vivo decomposition time of the tissue regenerating instrument A produced from the precursor to be controlled. Examples of the crosslinking method include chemical crosslinking with crosslinking agents, γ-ray irradiation, ultraviolet ray irradiation, electron beam irradiation, plasma irradiation, and thermal dehydration crosslinking. In particular, thermal dehydration crosslinking is preferred from the viewpoint of safety when implanted in a living organism. The condition of thermal dehydration crosslinking is such that the crosslinking temperature is about 100° C. to about 140° C. and the crosslinking time is 6 to 72 hours. In particular, from the viewpoint of crosslinking efficiency and suppressing thermal decomposition, the crosslinking temperature is about 110° C. to about 130° C., and the crosslinking time is 12 to 48 hours.

<Collagen Rod>

In the lumen of the tube 1, a rod 21 in a non-swelled state is provided. "Rod" refers to a foothold that induces growth of cells of the damaged tissue to grow in the longitudinal direction. The form of the foothold is, for example, a bundle of a plurality of threads made of a biodegradable material arranged substantially in parallel having a rod-like appearance. "Filament bundle" refers to a thing constituted by threads made of a biodegradable material, in which all the threads are arranged substantially in parallel to the longitudinal direction of the tube 1 and adjacent threads are adhered to each other. "Thread" is a collective term for a monofilament or a twist yarn. In particular, the thread is preferably a monofilament from the viewpoint of low production cost. Monofilament can be produced in the same production method as the monofilament that constitutes the tube 1.

The occupied cross-sectional area in a direction perpendicular to the longitudinal direction of the rod 21 in a non-swelled state is smaller than the cross-sectional area of the lumen of the tube 1. For example, assuming the cross-sectional area of the lumen of the tube 1 is taken as 100, a ratio of the occupied cross-sectional area in a direction perpendicular to the longitudinal direction of the tube 1 is set to 5 to 10. Accordingly, the amount of the material of filament bundle is requisite minimum, so that the cost of the material can be suppressed. "Occupied cross-sectional area" refers to an area of a figure surrounded by an outermost peripheral line around the rod on a plane perpendicular to the longitudinal direction of the rod 1 and a void in the area is not taken into consideration. For example, when the rod 21 of the present invention is a filament bundle, a gap invariably occurs between a plurality of threads that constitute the filament bundle. It is obvious that even in the case of hexagonal closes packing, which is the closest state, the gap invariably, occurs between the pluralities of threads that constitute the filament bundle. However, "Occupied cross-sectional area" refers absolutely to an area of surface surrounded by line of periphery of filament bundle and gap is not taken into consideration.

The occupied cross-sectional area perpendicular to the longitudinal direction of the rod 21 is smaller than the cross-sectional area of the lumen of the tube, in other words, a state where the rod 21 is localized on the inner wall of the tube 1. Therefore, the occupied cross-sectional area of the rod 21 is smaller than the lumen cross-sectional area of the tube 1, so that the operation of inserting the rods 21 in the lumen of the tube 1 is easy. Further, the tube 1 after the rod 21 is inserted therein has a longitudinal space, so that in the swelling operation described hereinbelow, the softening solvent can sufficiently penetrate into the inside of the tube to uniformly swell the rod 21. In addition, the penetration of the softening solvent into the precursor B is sufficiently fast, the time of swelling operation at the site of surgical operation can be shortened. In the present invention, the "space having a longitudinal direction" is also referred to a "fluid passage".

Figure 4:
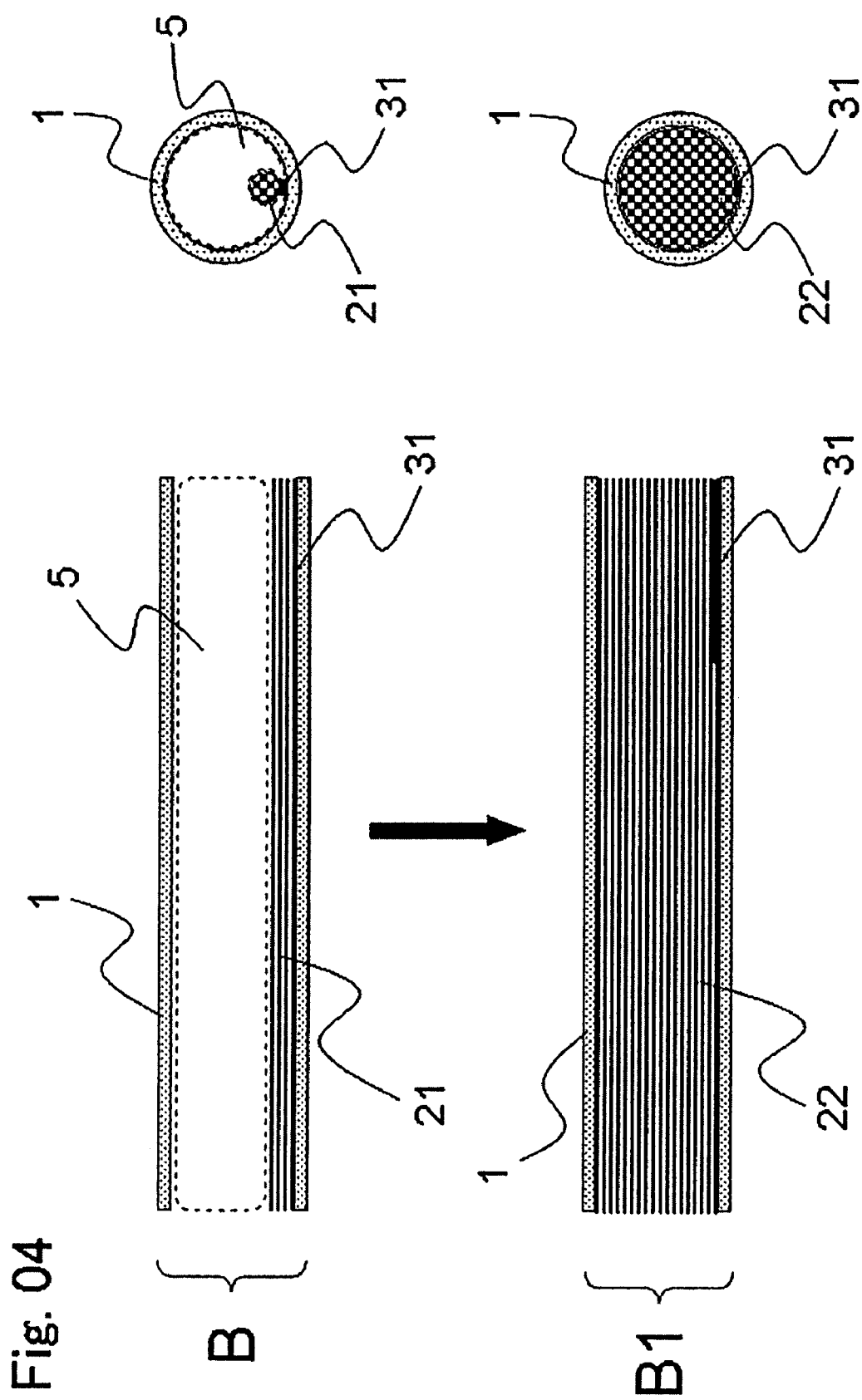
FIG. 4 is a diagram illustrating a step of swelling the precursor B of the tissue regenerating instrument of the present invention with a softening solvent.

The occupied cross-sectional area in a plane perpendicular to the longitudinal direction of the rod 22 in a saturated swelling state by the swelling described hereinafter is substantially the same as the lumen cross-sectional area of the tube 1 (FIG. 4). Substantially the same means to such an extent that assuming the lumen cross-sectional area of the tube 1 is 100, a ratio of the occupied cross-sectional area of a plane perpendicular to the longitudinal direction of the tube 1 to the lumen cross-sectional area of the lumen 1 is 90 to 100. In other words, the rod 22 in a saturated swelled state contacts the lumen of the tube 1 such that the rod 22 will not drop out from the lumen of the tube 1 and further that the occupied volume of the fluid passage 5 is extremely decreased by swelling of the rod 21, preferably to such an extent that there is no fluid passage 5 itself. The occupied cross-sectional area is treated to have the same meaning as described above. The ratio is a value obtained by swelling in a softening solvent such as physiological saline as is, with the rod being not inserted in the lumen of the tube 1. That is, the occupied cross-sectional are of the rod 22 is in a saturated swelled state is substantially the same as the lumen cross-sectional area of the tube 1, so that the tube 1 is neither deformed nor broken. Further, the rod 22 in a saturated swelled state can slide in the lumen of the tube 1 in such a state that an appropriate wetting and friction resistance exist between the inner wall of the tube 1 and the rod 22 in a saturated swelled state.

Here, depending on the material of the rod 22, the occupied volume of the rod 22 in a saturated swelled state at a temperature (at about 25° C.) at which the rod is allowed to swell in a softening solvent and the occupied volume of the rod 22 in a saturated swelled state at a temperature (about 37° C.) at which the rod 22 is implanted in a living organism may differ. In such as an occasion, the swelling property of the rod 21 can be appropriately set, for example, such that the ratio of the occupied cross-sectional area of the plane perpendicular to the longitudinal direction to the lumen cross-sectional area of the tube 1 being taken as 100 is 90 to 95 at a temperature (about 25° C.) at which the rod 22 is swelled in the softening solvent or 96 to 100 at a temperature (about 37° C.) at which the rod 22 is implanted in a living organism.

The appearance configuration of the rod 21 is not particularly limited and may be, for example, a tetragonal prism, a trigonal prism or a circular column. However, taking into consideration that the occupied cross-sectional area of the tube 1 in a plane perpendicular to the longitudinal direction of the rod 22 in a saturated swelled state is substantially the same as the lumen cross-sectional are of the tube 1, the shape of the rod 21 is preferably the same shape as that of the tube 1. For example, when the tube 1 is cylindrical, preferably the rod 21 is also circular column.

The method of forming a filament bundle is exemplified by a method in which after a wet spinning is performed, the monofilament is wound around a tetragonal plate or frame with at least opposing two sides being parallel such that the monofilament is substantially perpendicular to the two sides and the wound up monofilament is cut near the two sides to obtain a filament bundle. The speed of winding up by the plate or frame can be the same as the above-mentioned conditions under which the tube is produced from the monofilament. A filament bundle is obtained by binding up a plurality of threads such that the ratio of the occupied cross-sectional area is perpendicular to the longitudinal direction of the filament bundle to the lumen cross-sectional area of the tube 1 being taken as 100 is about 5 to about 10. Making the ratio of the occupied cross-sectional area perpendicular to the longitudinal direction of the filament bundle to the lumen cross-sectional area of the tube 1 being taken as 100 about 5 to about 10 can be achieved, for example, by binding up about 200 to about 250 monofilaments having an outer diameter of about 50 μm to a tube having an inner diameter of about 3.0 mm. Since the monofilaments inserted in the lumen of the tube 1 take an outer diameter of about 200 μm in a saturated swelled state, the occupied cross-sectional area of the filament bundle to the lumen cross-sectional are being taken as 100 is 90 to 100.

Thereafter, adjacent threads are adhered to each other to obtain the rod 21. The method of adhering can be, for example, a method in which a filament bundle is immersed in a solution of a biodegradable polymer and then dried. When the thread is a monofilament made of a crosslinked collagen, a method in which the filament bundle is immersed in water is exemplified. The crosslinked collagen, when immersed in an aqueous solution, is slightly dissolved around the collagen monofilament. The dissolved collagen attaches to adjacent contacting collagen monofilaments, so that drying completes the adhesion. The aqueous solution in which the filament bundle is immersed is not particularly limited and includes water itself. In particular, when the threads are obtained from acid- or alkali-soluble collagen and the monofilament is a crosslinked one, the filament bundle obtained by the above-mentioned method has not been subjected to neutralization treatment, so that a neutralization solution can be selected as the aqueous solution. The neutralization solution can be selected as appropriate by one skilled in the art. For example, the filament bundle obtained by binding up collagen monofilaments obtained by acid-soluble collagen can be neutralized with a basic aqueous solution such as a calcium hydroxide aqueous solution, a potassium hydroxide aqueous solution or a sodium hydrogen carbonate (baking soda) aqueous solution to have adjacent threads in the filament bundle partly adhered to each other.

From the viewpoint of facilitating production of a tissue regenerating instrument A provided with a tissue insertion space 4 for inserting a tissue at both ends, which is an object of the present invention, it is preferable that the longitudinal length of the rod 21 is shorter than the longitudinal length of the tube 1 by the tissue insertion space forming length (D) and in this state, one end of the tube 1 and one end of the rod 21 are aligned. "Tissue insertion space forming length" refers to a length necessary for providing the tissue insertion space 4 on both ends. Hereinafter, the tissue insertion space forming length may be abbreviated as D. While a specific length may be determined by one skilled in the art as appropriate depending on the tissue to be regenerated and is not particularly limited, the specific length can be about 2 to about 4 folds of the longitudinal length of the tissue insertion space 4. In particular, from the viewpoint of providing on both ends and facilitating insertion of tissues, the length of the tissue insertion space forming length is preferably about 2 folds of the longitudinal length of the tissue insertion space 4, that is 4 mm to 40 mm. Since aligning one end of the tube 1 and one end of the rod 21 to each other provides a flat end surface. Hence in the present invention, the aligned ends are also called "flat ends". On the other hand, along with this, one end of the tube 1 and one end of the rod 21 are not aligned at the other end of the precursor B and form a space. Hence, in the present invention, this space is also referred to as "space portion".

<Fixing Means>

The thus obtained rod 21 is inserted in the lumen of the tube 1. Since the ratio of the occupied cross-sectional area perpendicular to the longitudinal direction of the rod 21 to the lumen cross-sectional area of the tube 1 being taken as 100 is about 5 to about 10, this operation is very easy. However, when the rod 21 is merely inserted in the lumen of the tube 1, the rod 21 is slipped out of the lumen of the tube 1 and the rod 21 will be contaminated.

For example, the collagen body disclosed in Patent Document 2 is not fixed to the tube, so that the collagen body slides in the tube. When transported or in use, the collagen body may be dropped out and contaminated.

On the other hand, to solve the problem, it is conceivable to densely fill the collagen body disclosed in Patent Document 2 in the lumen of the tube. However, the tube may be deformed due to swelling with the softening solvent used before implantation of the tube in the tissue.

Similarly, the fiber made of a synthetic bioabsorbable polymer disclosed in Patent Document 3 is not fixed to the tube but the filament bundle slides in the tube. Therefore, similar problems as those of Patent Document 2 are encountered.

In the case of the invention disclosed in Patent Document 3, it is conceivable to densely fill the fiber made of a synthetic bioabsorbable polymer in the lumen of the tube. However, the tube may be deformed due to swelling with the softening solvent used before implantation of the tube in the tissue.

To avoid the adverse effect, in the present invention, there is provided a fixing means 31, 32 that fixes the rod 21 to the tube 1. However, upon producing the organ regenerating instrument A from the precursor B, mere provision of the fixing means 31, 32 does not enable production of the tissue regenerating instrument A provided with the tissue insertion space 4 for inserting a tissue on both ends thereof, which is an object of the present invention.

For example, the instrument disclosed in Patent Document 4 is cut according to the length of the nerve to be regenerated and the nerve end on the side of a central nerve is inserted into the space portion to effect implantation. Although, it cause no problem of dropping out of the matrix and/or nerve guidepath when transported or in use since the matrix and/or a nerve guidepath is fixed to the tube, there arises the problem that end-to-end suture must be performed since a flat end is formed on the peripheral nerve side.

From the above, the precursor B of the present invention is provided with the fixing means 31, 32 for fixing the rod 21 to the tube 1. The fixing means 31, 32 are made of a material or of a structure such that upon production or transport of the precursor B. On the other hand, the fixation is released and the rod 22 in a saturated swelled state can slide in the lumen of the tube 1 when the rod 21 is fixed to the tube 1 but upon production of the organ regenerating instrument A from the precursor B.

As a first embodiment that satisfies the above conditions, an embodiment that the fixing means 31 is arranged at a position to be excised and firmly fixed is exemplified in an adjustment of the length of the tissue regenerating instrument A produced from the precursor B. That is, as illustrated in FIG. 2, this embodiment is one in which the fixing means 31 is provided on a portion of the inner wall of the excised region of the tube 1. "Excised portion of tube" refers to a portion of the precursor B to be excised upon adjustment of the length of the precursor B. More particularly, the excised portion of tube is a region in a range of length of a ratio of 0.01 to 50% from one end when the longitudinal length of the tube 1 is taken as 100%. That is, at most one region from the midpoint of the longitudinal length of the tube 1 toward one end of the tube 1. However, in order for the precursor B to be able to produce a tissue regenerating instrument A that can be applied to regeneration of a long tissue, it is important that the excised portion is minimum, and the excised portion is a region in a range of ratio of length of preferably 0.01 to 30%, particularly preferably 0.01 to 10%. That is, when a portion of the precursor B including the fixing means 31 is excised, the rod 22 in a saturated swelled state becomes slidable in the lumen of the tube 1.

As the fixing means 31 in the first embodiment above, for example, any one selected from the group consisting of a thread, a stapler, an adhesive, and combinations thereof are exemplified. Fixing with the thread or stapler is achieved by penetrating the rod 21.

"Adhesive" refers to a substance that is present between the tube 1 and the rod 21 and bonds them together through anchoring effect, physical adsorption, covalent bond, ionic bond, hydrophobic bond, coordination bond, and hydrogen bond. As the adhesive, one that is scarcely soluble in water and has excellent storage stability is selected as appropriate. For example, polymer compositions containing a nonbiodegradable polymer such as acrylic resins and fluorinated resins, biodegradable polymers such as crosslinked collagen, polylactate and homopolymers of hydrophobic amino acids may be exemplified. In particular, while the fixing means 31 is cut off in the adjustment of the length of the precursor B, if the adhesive remains, the adhesive must be safe to the living organism. Taking this into consideration, the adhesive is preferably biodegradable polymers such as crosslinked collagen, polylactate and homopolymers of hydrophobic amino acids, more preferably crosslinked collagen.

As a second embodiment, an embodiment in which the fixing means 32 is releasable is exemplified. In this case, the position of the fixing means 32 is not particularly limited. The fixing means 32 in this embodiment is any one selected from the group consisting of, for example, a thread, a stapler, a binder and combinations thereof. Fixing with a thread or stapler can be made by penetrating the rod 21 from the outer wall of the tube 1. The release of the fixing means 32 may be achieved by physically removing the fixing means 32 as is.

On the other hand, "binder" refers to a substance that bonds the tube 1 and the inducing member (i.e., rod) 21 to each other, but that can release the binding by dissolving in a good solvent of the polymers constituting itself. In the present invention, such a good solvent is termed as a binder solvent. However, the binder solvent should not dissolve the precursor B itself during the treatment, the binder solvent must be a poor solvent to the biodegradable polymer that constitutes the precursor B.

Therefore, if the binder solvent is determined, the polymer constituting the binder can be selected with ease. For example, in the case where the biodegradable polymer is collagen and the collagen is crosslinked, almost all solvents can be applied excluding strong acids or strong alkalis that decompose the main skeleton of the collagen. Specific examples of the solvent include water, methanol, ethanol, acetone, hexane, benzene, xylene, 1,2-dichloromethane, chloroform, tetrahydrofuran, and dimethyl sulfoxide. In particular, form the viewpoint that if the solvent is remained in the instrument after the treatment, the living organism is not affected, water is preferable. However, the present invention is not limited thereto.

Water includes city water, distilled water, reverse osmotic water, deionized water, and so on. Further, water may contain physiologically acceptable salts. That is, physiological saline can be used. Here, the tissue regenerating instrument A is swelled with a softening solvent in order to increase handleability in suturing upon implantation. As the softening solvent, physiological saline is generally used. Accordingly, the water is preferably physiological saline from the viewpoint that the step of swelling the precursor B of the present invention and the step of releasing the binder can be performed simultaneously.

For example, in the case where the biodegradable polymer is crosslinked collagen and physiological saline is used as the binder solvent, such a polymer constituting the binder is not particularly limited as far as the polymer is a hydrophilic polymer. Examples of such a hydrophilic polymer include non-crosslinked collagen, polylysine, polyglutamate, polyethylene glycol, and glycosaminoglycans such as alginic acid, chitosan, hyaluronic acid and chondroitin sulfate. In particular, in the case where the material that constitutes the tube 1 and the rod 21 are crosslinked collagen, non-crosslinked collagen is preferable from the viewpoint of high adhesion with the crosslinked collagen and no affection on the living organism if remained in the precursor B after the treatment.

<Production of Tissue Regenerating Instrument>

Hereinafter, the method of producing a tissue regenerating instrument A from a precursor B of the tissue regenerating instrument of the present invention is described referring to the attached diagram illustrating. Note that the precursor B of the tissue regenerating instrument is wholly made of collagen and the fixing means 31 is a non-crosslinked collagen binder. However, the present invention should not be considered as being limited thereto as described above.

The production method of tissue regenerating instrument A of the present invention includes:
(1) immersing the precursor B of the tissue regenerating instrument in a softening solvent to swell the precursor B;
(2) releasing the fixing means 31, 32 to make the rod 22 in a saturated swelled state slidable in the inner lumen of the tube 1;
(3) excising a portion of the precursor B, so that the longitudinal length of the precursor B is a sum of a length of a tissue to be regenerated and a tissue insertion space forming length (D);
(4) excising a portion of the rod 22 to make a longitudinal length of the rod 22 in a saturated swelled state than a longitudinal length of the tube 1 by a tissue insertion space forming length (D); and
(5) arranging the rod 22 in the center of the tube 1 to form a tissue insertion space 4 in a lumen on both ends of the tube 1.

(1) Step of Immersing a Precursor B of a Tissue Regenerating Instrument in a Softening Solvent to Swell the Precursor B First, a precursor B of the tissue regenerating instrument of the present invention is immersed in a softening solvent to soften the precursor B in order to increase the handleability of suture upon implantation. As the softening solvent, mainly physiological saline is used. However, the present invention is not limited thereto. The conditions are atmospheric pressure, a humidity of 60%, and a softening solvent at 25 to 40° C.

(2) Releasing the Fixing Means 31, 32 to Make the Rod 2 Slidable in the Lumen of the Tube 1

This step (2) differs in content depending on the embodiment of the fixing means 31, 32. For example, the fixing means 31, 32 are in a first mode, that is, in a mode in which the fixing means 31 is arranged in the excision region of the tube 1. In this mode, the step (2) is performed together with the step (3) described hereinafter. This is because in the step (3) described hereinafter, the fixing means 31 arranged in the excised region of the tube 1 is excised.

For example, the fixing means 32 is in a second mode, namely, releasable, the fixing means 32 in the second mode can be removed as is.

Further, for example, in the case where the softening solvent is physiological saline and the fixing means 32 in the second mode is the above-mentioned binder, the fixing means 32 can be released by treating the fixing means 32 with the binder solvent. In particular, when the binder is a hydrophilic polymer that is soluble in water, the hydrophilic polymer is dissolved in physiological saline in the above-mentioned step (1), so that this step (2) can be omitted and thus is preferable.

In the precursor B in which the fixing means 31, 32 are released or excised after swelling, friction resistance is generated between the tube 1 and the rod 22 in a saturated swelled state. Further, the occupied cross-sectional area of the rod 22 in a saturated swelled state is substantially the same as the lumen cross-sectional area of the tube. Accordingly, the rod 22 in a saturated swelled state can slide in the lumen of the tube 1 but will not slip out of the lumen.

(3) Excising a Portion of the Precursor B1, so that the Longitudinal Length of the Precursor B1 is a Sum of the Length of a Tissue to be Regenerated and a Tissue Insertion Space Forming Length (D)

Figure 5:
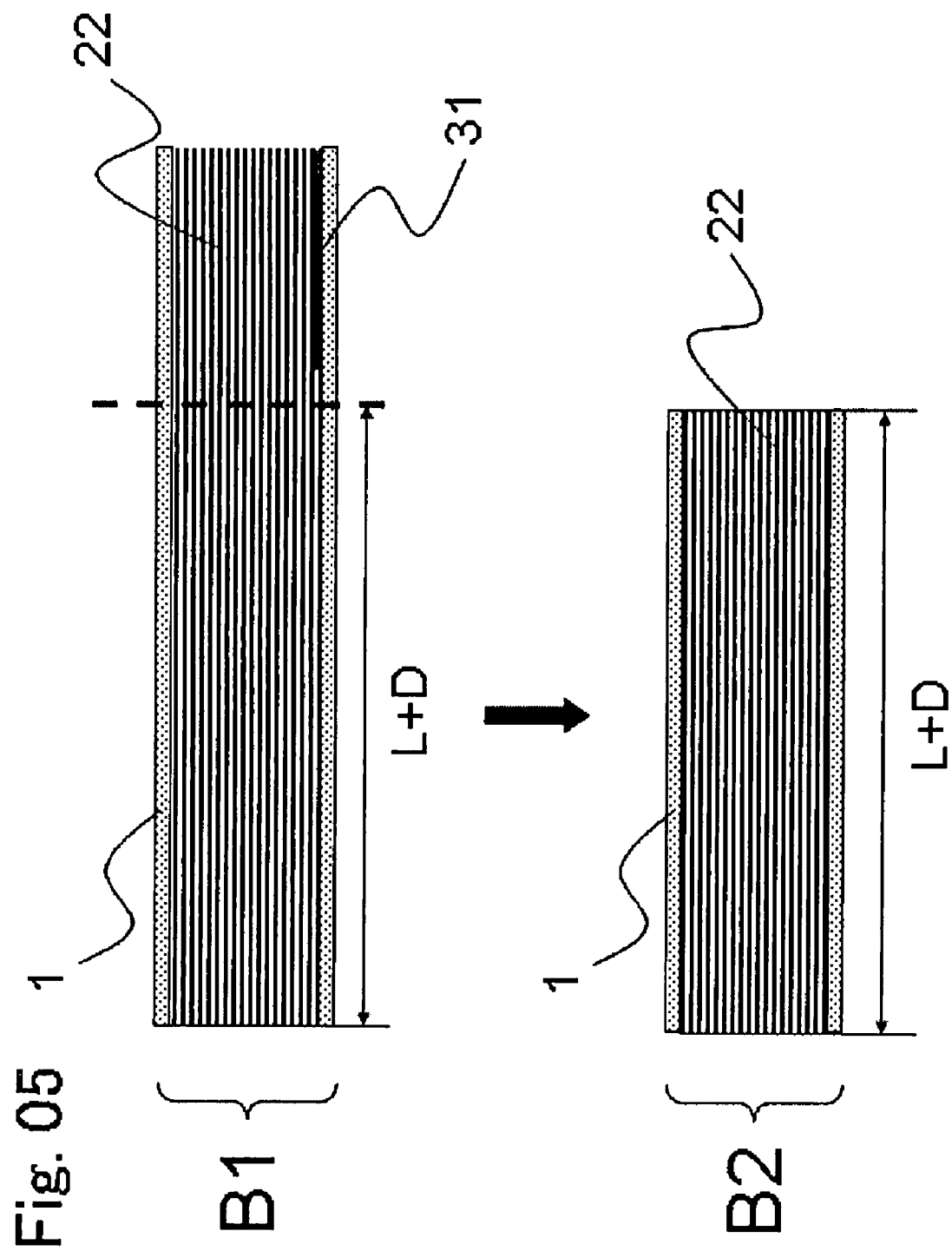
FIG. 5 is a diagram illustrating a step of excising the precursor B1 of the tissue regenerating instrument shown in FIG. 4.

Next, a portion of the precursor B1 is excised depending on the length of a tissue to be regenerated to adjust the length of the precursor B1. Specifically, the precursor B1 is excised such that the longitudinal length of the precursor B1 is the sum of the length of the tissue to be regenerated (hereinafter, in some cases abbreviated as L) and the tissue insertion space forming length (D) (FIG. 5: B1 to B2). For example, assuming that the tissue to be regenerated is nerve, the length (L) of the nerve to be regenerated is 100 mm, and the tissue insertion space forming length is 20 mm, then the precursor B2 is excised such that the length of the precursor B2 is 120 mm. Excision is can be performed by using a cutting instrument such as scissors, microtome or a surgical knife. Note that the length of the precursor B corresponds to the length of the tissue to be regenerated before this step (3) is performed, this step is deemed to have been performed with doing nothing particular.

Further, the fixing means 31 is in the first mode, that is, in the case where the fixing means 31 is arranged in the excision region of the tube 1, the step (3) can be performed simultaneous with the step (2). In this case, in the steps (2) and (3), even if the fixing means 31 remains after all efforts, the fixing may be released by pressing the rod 22 in a saturated swelled state in the longitudinal direction because the remaining amount of the fixing means 31 is small.

(4) Excising a Portion of the Rod 22 in a Saturated Swelled State to Make the Longitudinal Length of the Rod 22 in a Saturated Swelled State is Shorter than the Longitudinal Length of the Tube 1 by a Tissue Insertion Space Forming Length (D)

Figure 6:
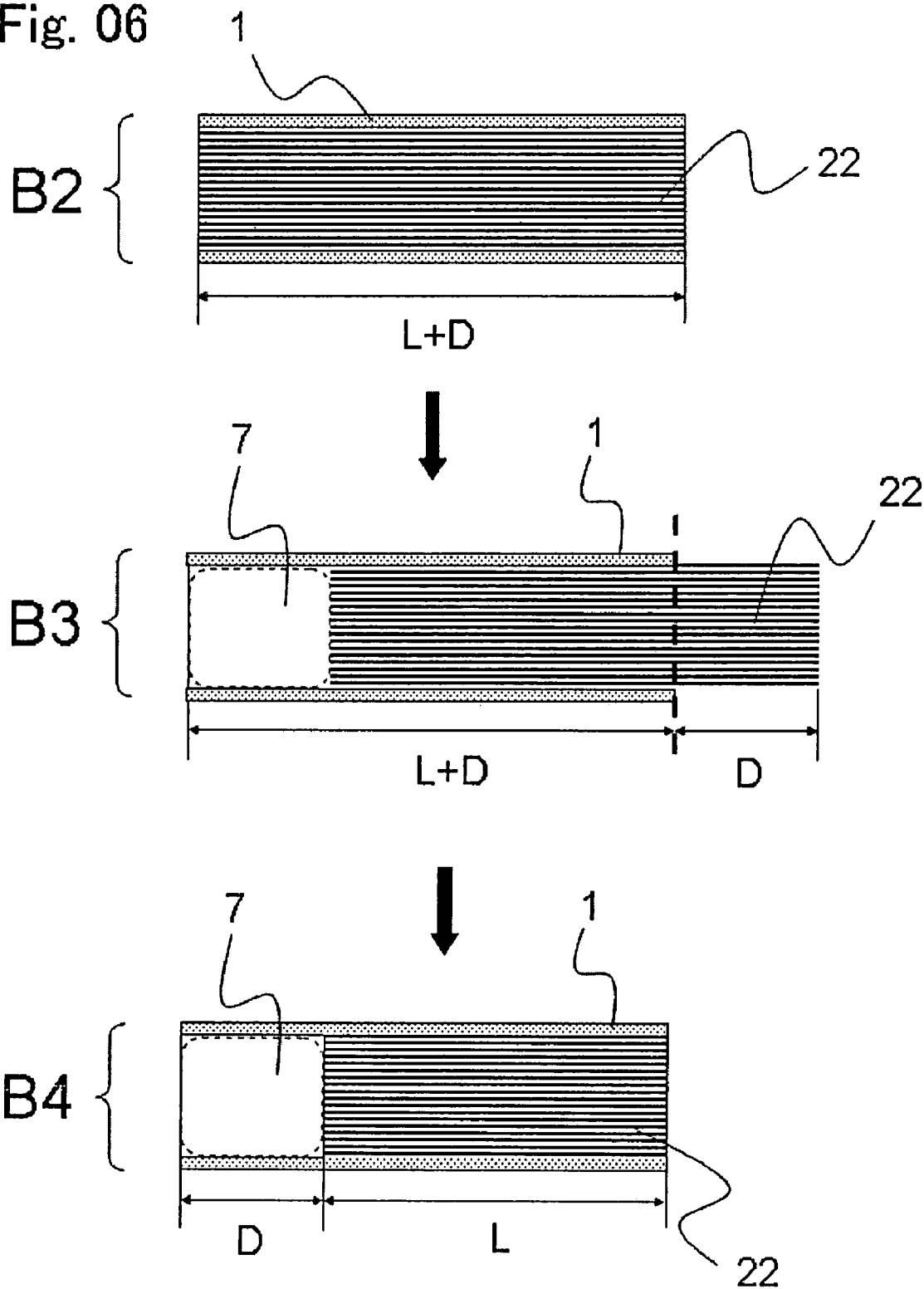
FIG. 6 is a diagram illustrating a step of sliding and protruding a rod 22 in a saturated swelled state from the precursor B2 of the tissue regenerating instrument after the step shown in FIG. 5 and then excising the protruded portion.

Then, the rod 22 in a saturated swelled state is slided in the lumen of the tube 1 so as to protrude from one end of the tube 1 by the tissue insertion space forming length (D) (FIG. 6: B2 to B3). The longitudinal length of the rode 22 in a saturated swelled state is adjusted by excising the protruded portion (FIG. 6: B3 to B4). This length is substantially the same as the length of the tissue from which the affected site has been excised. For example, assuming that the tissue to be regenerated is nerve, the tissue insertion space forming length (D) is 20 mm, and the length of the precursor B2 is 120 mm, then the longitudinal length of the rod 22 obtained by the above-mentioned operation (L: length of the nerve to be regenerated) is 100 mm.

Figure 3:
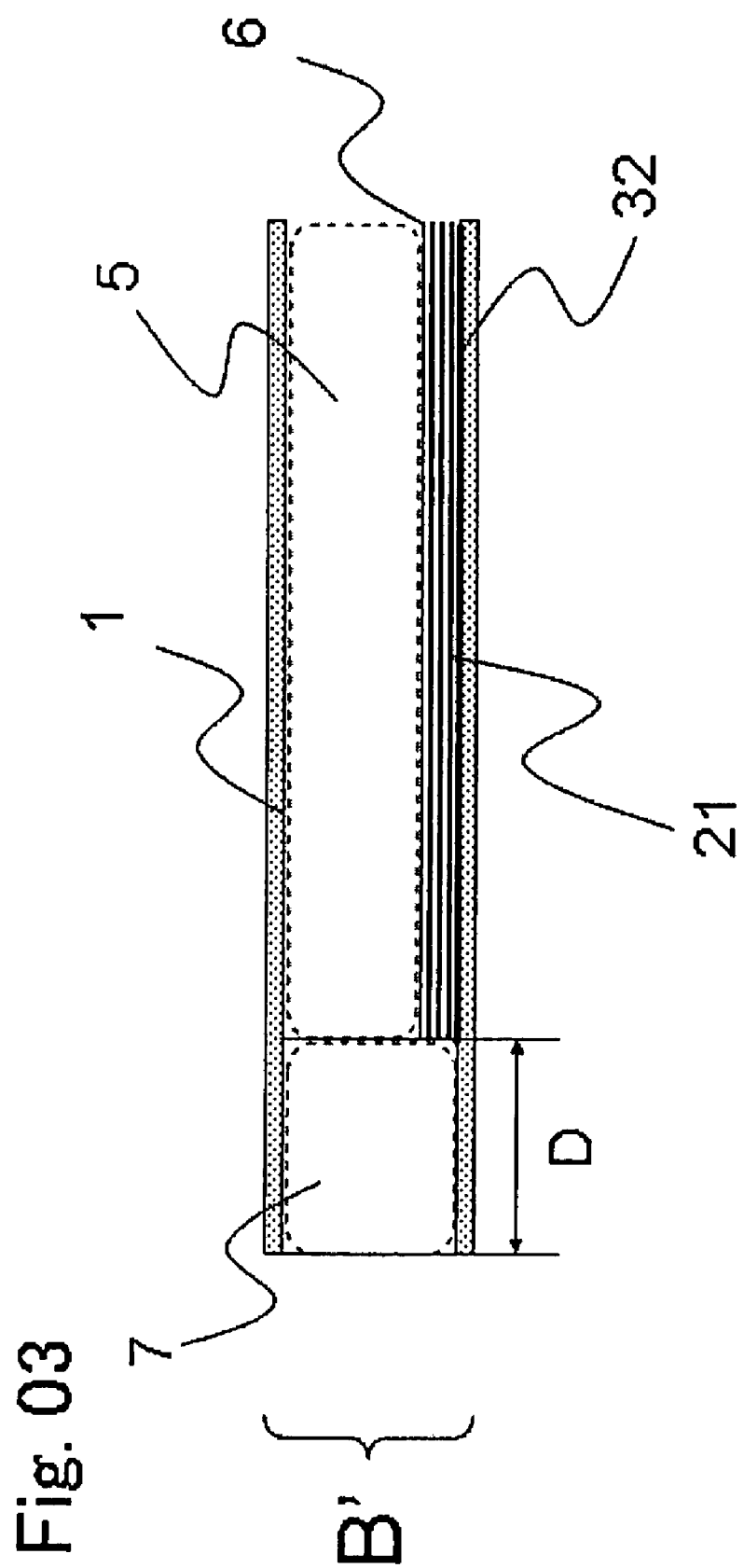
FIG. 3 is a diagram illustrating a variation (B') of the precursor of the tissue regenerating instrument of the present invention.
Figure 7:
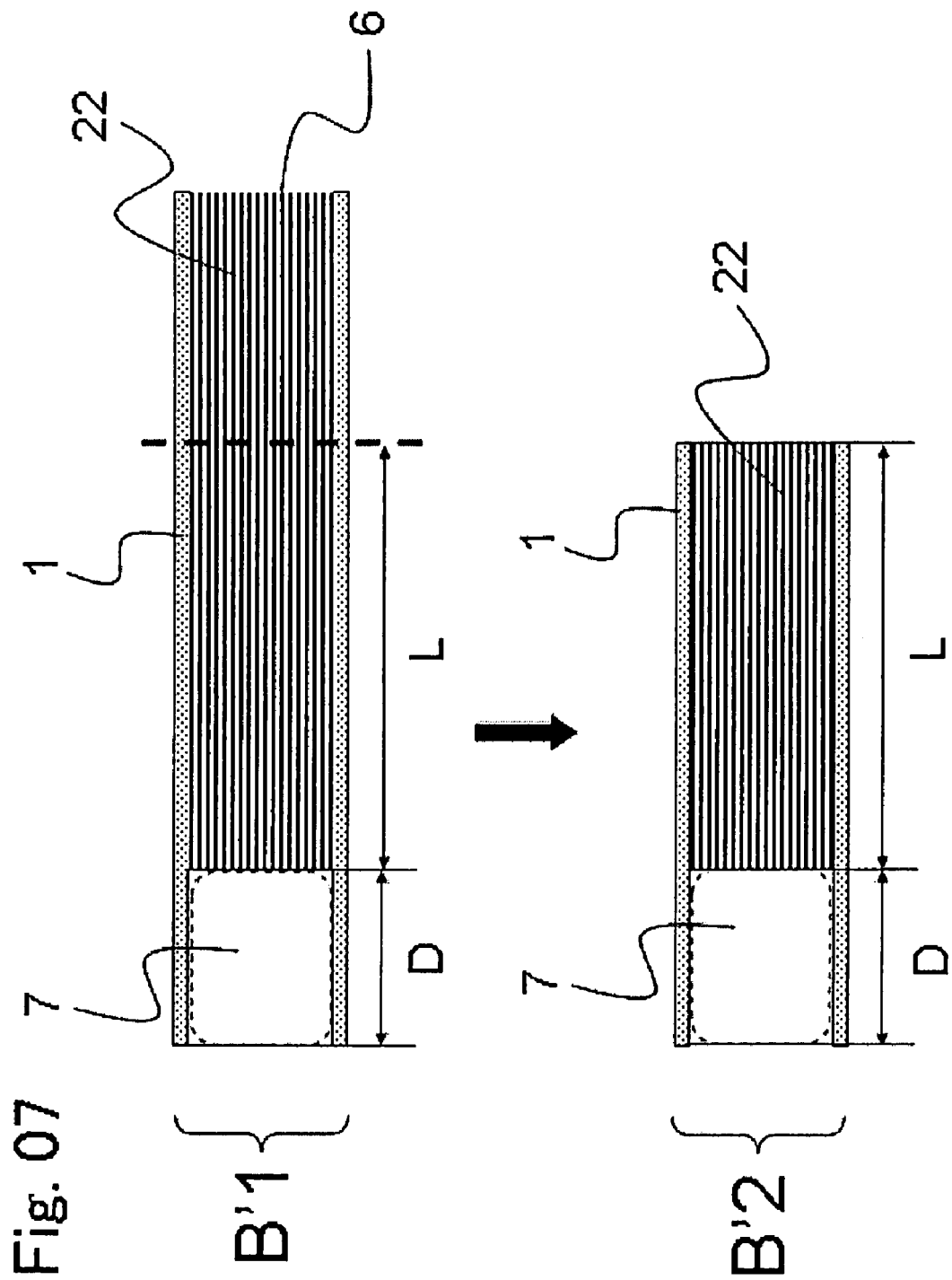
FIG. 7 is a diagram illustrating a step of excising the precursor B'1 of the tissue regenerating instrument shown in FIG. 3 swelled with a softening solvent.

In this case, in a structure in which as illustrated in FIG. 3, the longitudinal length of the rod 2 is shorter than the longitudinal length of the tube 1 by the tissue insertion space forming length (D), and one end of the tube 1 and one end of the rod 2 are aligned (a structure provided with a flat end 6 and a space portion 7), excising a portion of the precursor B on the side of the flat end 5 in the above-mentioned step (2) results in that the present step is simultaneously performed and thus is preferable (FIG. 7: B1' to B2').

(5) Arranging the Rod 22 in the Center of the Tube 1 to Form a Tissue Insertion Space 4 in a Lumen on Both Ends of the Tube 1

Figure 8:
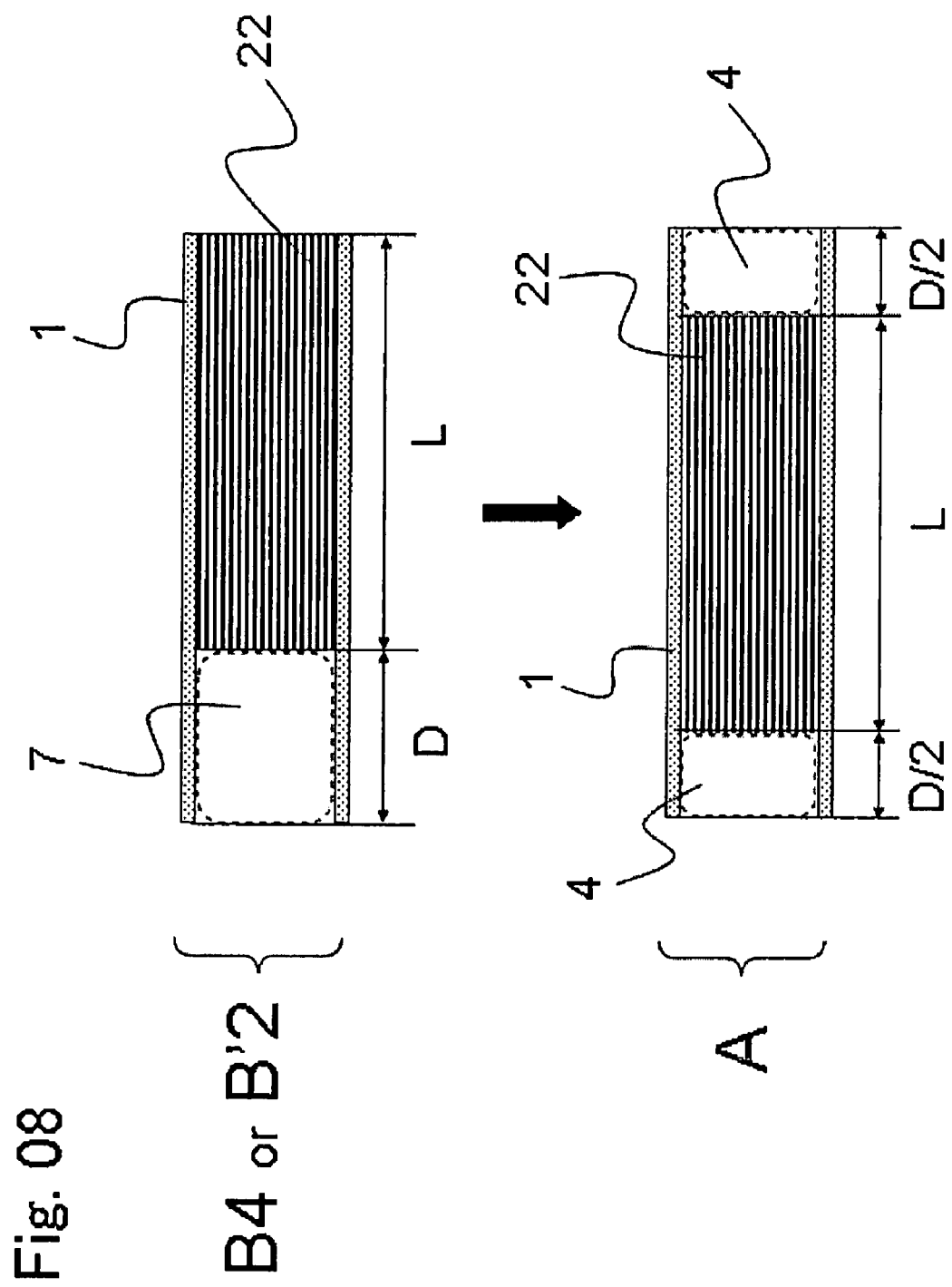
FIG. 8 is a diagram illustrating a step of sliding the rod 22 in a saturated swelled state and providing a tissue insertion space 4 at both ends after the step shown in FIG. 6 or FIG. 7.

Thereafter, when the rod 22 is slided such that the longitudinal midpoint of the rod 22 in a saturated swelled state and the longitudinal midpoint of the tube 1 are arranged to coincide with each other, the tissue insertion space 4 having a longitudinal length half the tissue insertion space forming length (D) (D/2) can be formed at both ends (FIG. 8: B4 to A, or B'2 to A).

As described above, the tissue regenerating instrument A produced from the precursor B of the tissue regenerating instrument of the present invention can be implanted only by inserting tissue ends since the tissue regenerating instrument A is provided with the tissue insertion space 4 on both ends thereof, so that implantation operation can be readily performed without performing suture. Further, the bad effect that cells grow on the outer surface of the tube 1 can be prevented.

EXAMPLE

Hereinafter, examples of the present invention are described. However, the present invention should not be considered to be limited thereto.

Example 1

Production of Precursor B of Tissue Regenerating Instrument (1) Production of Tube 1
Enzyme-solubilized collagen was dissolved in water to prepare a 5% (w/w) aqueous solution. The collagen solution was discharged in a 99.5% (v/v) ethanol coagulation bath to spin a collagen monofilament having a diameter of about 200 μm. The collagen monofilament drawn up from the ethanol coagulation bath as it was wound around a cylindrical mold made of a polyfluoroethylene fiber having an outer diameter of 3.0 mm at a speed of about 4,000 m/min and dried. Then, the product was immersed in a 5% (w/w) collagen aqueous solution and dried to form the innermost layer of the tube 1. Further, the collagen monofilament was again wound around an outer periphery of the innermost layer of the tube 1 at a speed of about 4,000 m/min and the resultant was subjected to thermal dehydration crosslinking reaction in a vacuum dry oven (manufactured by EYELA Co., VOS-300VD Model) under reduced pressure (1 torr or less) at 120° C. for 24 hours. The obtained collagen tube was again immersed in a 5% (w/w) collagen aqueous solution and dried, and then subjected to the thermal crosslinking reaction to produce a tube 1 made of crosslinked collagen having an inner diameter of 3.0 mm, an outer diameter of 3.3 mm, and a length of 70 mm.

(2) Production of Rod 2
In the above-mentioned wet spinning using an ethanol coagulation bath, the monofilament drawn up from the coagulation bath was wound around a frame having a rectangular shape of about 150 mm×150 mm under conditions of a temperature of about 25° C. and humidity of 50% or less while performing air blasting drying. On this occasion, the spinning speed was about 4,000 m/min. Then, the monofilament in a state wound around the frame was subjected to thermal dehydration crosslinking reaction in a vacuum dry oven (manufactured by EYELA Co., VOS-300VD Model) under reduced pressure (1 torr or less) at 120° C. for 24 hours. Then the wound filament was cut to a length of about 50 mm and bound to produce a cylindrical column having an outer diameter of about 1.0 mm. The cylindrical bundle was impregnated in a 7.5% (w/w) sodium hydrogen carbonate aqueous solution and dried to prepare a rod 21 having an outer diameter of about 1.0 mm and a length of 50 mm made of a filament bundle of monofilaments made of crosslinked collagen. The longitudinal length of the rod 21 was shorter than the longitudinal length of the tube 1 by 20 mm. That is the tissue insertion space forming length (D) was 20 mm. Assuming the lumen cross-sectional area of the tube 1 is 100, the ratio of the cross-sectional area of the rod 21 perpendicular to the longitudinal direction of the rod 21 to the cross-sectional are of the tube 1 was about 11.1.

(3) Production of a Precursor B of the Tissue Regeneration Instrument Shown in FIG. 3
On a region of 5 mm from one end of the rod 21 made of the cross-linked collagen was coated with a 5% (w/w) collagen aqueous solution. Then, the rod 21 was inserted into the lumen of the tube 1 such that one end of the rod 21 coated with the collagen aqueous solution was aligned with one end of the tube 1. In this state, thermal dehydration crosslinking reaction was allowed to proceed to fix the rod 2 to the tube 1 with the adhesive 31 of crosslinked collagen to obtain a precursor B of the tissue regenerating instrument as shown in FIG. 4. That is, in the lumen on one end of the tube 1, the rod 21 is present and a flat end 6 is formed while in the lumen on the other end of the tube 1, the rod 21 is absent and a space portion 7 is formed. The thus-obtained precursor B was subjected to 25 kGy γ-ray sterilization treatment.

Example 2

Production of a Tissue Regenerating Instrument A

The precursor B of the tissue regenerating instrument obtained in Example 1 was immersed in physiological saline under atmospheric pressure, at a humidity of 60% and 25° C. for 20 minutes to render the precursor B of the instrument in a saturated swelled state. Then, at a position of 20 mm from the flat end 5, the precursor B'1 containing the fixing means 31 was excised using a microtome (FIG. 7: B'1 to B'2). That is, the longitudinal length of the tube 1 was 50 mm, the longitudinal length of the rod 22 in a saturated swelled state (L: length of tissue to be regenerated) was 30 mm. Thereafter, in the lumen of the tube 1, the rod 22 in a saturated swelled state was slided by 10 mm to locate the rode 22 substantially in a central position to produce a tissue regenerating instrument A provided with a tissue insertion space 4 at both ends (FIG. 8: B'2 to A)

What is claimed is:
1. A precursor for producing a tissue regenerating instrument that regenerates a tissue, comprising:
a tube made of a biodegradable material provided with a lumen in a longitudinal direction;
a single rod made of a biodegradable material swellable with a softening solvent, localized and fixed to an inner wall of the tube substantially parallel to the longitudinal direction of the tube; and
an adhesive that fixes said single rod to the inner wall of the tube, wherein
the rod comprises a bundle of a plurality of threads made of a biodegradable material arranged substantially in parallel, at least portions of adjacent threads being adhered to each other, and in a non-swelled state has an occupied cross-sectional area perpendicular to the longitudinal direction that is smaller than a cross-sectional area of the lumen of the tube, the occupied cross-sectional area perpendicular to the longitudinal direction of the rod in a saturated swelled state with the softening solvent is substantially the same as the cross-sectional area of the lumen of the tube; and said adhesive being provided only on a portion of the inner wall of are ion of the tube in a range of length of a ratio of 0.01 to 50% from one end of the tube, when a longitudinal length of the tube is taken as 100%.

2. The precursor of a tissue regenerating instrument according to claim 1, wherein the softening solvent is physiological saline.

3. The precursor of a tissue regenerating instrument according to claim 1, wherein the rod is substantially a circular column.

4. The precursor of a tissue regenerating instrument according to claim 1, wherein the rod has a longitudinal length shorter than a longitudinal length of the tube by a tissue insertion space forming length (D), and wherein one end of the tube and one end of the rod are aligned with each other.

5. The precursor of a tissue regenerating instrument according to claim 1, wherein the adhesive is provided on at least a portion of the inner wall of a region to be excised of the tube.

6. The precursor of a tissue regenerating instrument according to claim 1, wherein the rod has a longitudinal length shorter than a longitudinal length of the tube by a tissue insertion space forming length (D), and wherein one end of the tube on a side of a region to be excised and one end of the rod are aligned with each other.

7. The precursor of a tissue regenerating instrument according to claim 1, wherein the adhesive comprises a hydrophilic polymer.

8. The precursor of a tissue regenerating instrument according to claim 1, wherein the adhesive comprises a biodegradable material.

9. The precursor of a tissue regenerating instrument according to claim 1, wherein the bundle of a plurality of threads is obtained by immersing the plurality of threads which are arranged substantially in parallel in a solution of a biodegradable polymer, and then drying.

10. The precursor of a tissue regenerating instrument according to claim 1, wherein the bundle of a plurality of threads is obtained by immersing the plurality of threads made of a crosslinked collagen which are arranged substantially in parallel in water, and then drying.

* * * * *